US 9,662,188 B2

(12) United States Patent
Laubersheimer et al.

(10) Patent No.: US 9,662,188 B2
(45) Date of Patent: May 30, 2017

(54) METHOD FOR PRODUCING A DENTAL RESTORATION PART AND CAD/CAM DEVICE (75) Inventors: Jürgen Laubersheimer, Buchs (CH); Wolfram Murr, Chur (CH); Gottfried Rohner, Altstätten (CH); Nadja Schlechtriemen, Eschen (LI)

(73) Assignee: Ivoclar Vivadent AG, Schaan (LI)

( * ) Notice: Subject to any disclaimer, the term of this patent is extended or adjusted under 35 U.S.C. 154(b) by 700 days.

(21) Appl. No.: 13/371,893

(22) Filed: Feb. 13, 2012

(65) Prior Publication Data

US 2012/0205828 A1 Aug. 16, 2012

(30) Foreign Application Priority Data

Feb. 14, 2011 (EP) .................................... 11154372

(51) Int. Cl.
*A61C 13/00* (2006.01)
*A61C 9/00* (2006.01)
*A61C 13/09* (2006.01)
*A61C 19/10* (2006.01)

(52) U.S. Cl.
CPC ........ *A61C 13/0004* (2013.01); *A61C 9/0053* (2013.01); *A61C 13/0013* (2013.01); *A61C 13/0019* (2013.01); *A61C 13/09* (2013.01); *A61C 19/10* (2013.01)

(58) Field of Classification Search
USPC ......................................................... 700/98
See application file for complete search history.

(56) References Cited

U.S. PATENT DOCUMENTS

| | | | |
|---|---|---|---|
| 5,759,030 A | 6/1998 | Jung et al. | |
| 5,766,006 A | 6/1998 | Murljacic | |
| 6,028,672 A * | 2/2000 | Geng | ............................ 356/602 |
| 6,208,813 B1 | 3/2001 | Carlsson et al. | |
| 6,322,728 B1 | 11/2001 | Brodkin et al. | |
| 7,086,863 B2 * | 8/2006 | Van der Zel | ............. A61C 5/10 264/19 |
| 7,708,557 B2 | 5/2010 | Rubbert et al. | |
| 8,267,683 B2 | 9/2012 | Inoue | |
| 9,008,417 B2 | 4/2015 | Rohner et al. | |
| 9,404,740 B2 | 8/2016 | Babayoff | |
| 2005/0170315 A1* | 8/2005 | Strobel et al. | ............. 433/203.1 |
| 2006/0177792 A1 | 8/2006 | Touchstone | |

(Continued)

FOREIGN PATENT DOCUMENTS

DE 102007034005 A1 1/2009
EP 1252867 B1 7/2005

(Continued)

*Primary Examiner* — Carlos Ortiz Rodriguez
(74) *Attorney, Agent, or Firm* — Ann M. Knab; Thad McMurray (57) ABSTRACT The invention relates to a method for producing a dental restoration part, in which method, geometrical data, in particular data with respect to spatial dimensions, position and/or volume of the restoration part, are determined and stored in order to form a virtual restoration part. In a further process step, the virtual restoration part is provided for the tooth (10) to be replaced by using data of the tooth (10) to be replaced, a neighboring tooth (60) and/or a tooth stump, and said data is stored as color data and is used for the computer-assisted production of the virtual restoration part.

24 Claims, 4 Drawing Sheets (56) References Cited

U.S. PATENT DOCUMENTS

| | | |
|---|---|---|
| 2007/0212667 A1 | 9/2007 | Jung et al. |
| 2009/0033927 A1 | 2/2009 | Kerschbaumer |
| 2009/0133260 A1 | 5/2009 | Durbin et al. |
| 2010/0106276 A1 | 4/2010 | Holzner et al. |
| 2010/0119996 A1 | 5/2010 | Kaigler, Sr. |
| 2010/0291505 A1 | 11/2010 | Rawley et al. |

FOREIGN PATENT DOCUMENTS

| | | |
|---|---|---|
| JP | 2005-059477 A | 3/2005 |
| WO | 2007/013240 A1 | 2/2007 |

* cited by examiner

METHOD FOR PRODUCING A DENTAL RESTORATION PART AND CAD/CAM DEVICE

CROSS-REFERENCE TO RELATED APPLICATIONS

This application claims the benefit of EP Patent Application No. 11154372.4, filed Feb. 14, 2011, which is hereby incorporated by reference in its entirety.

TECHNICAL FIELD

The present invention relates generally to a method and device for producing a dental restoration part and in particular using computer assisted manufacturing and a computer assisted manufacturing device to produce a dental restoration part.

BACKGROUND

It has been known for some time now that methods for producing dental restoration parts may be improved by determining the chroma and brightness values of neighboring teeth adjacent to the tooth to be restored, and are used as a model, also with respect to the local distribution, for the dental restoration part. Typically, the teeth are produced in different tooth colors wherein color sample denotations or "tooth colors" such as A2, B3 etc., are commonly used and set the tooth both with respect to brightness and the base color.

While an optical comparison by, for example, a color key or shade guide was traditionally conducted, as it is known from DE 10 2007 035 610 A1 and corresponding US published application No. 20090033927, which is hereby incorporated by reference, it has also been known for some time now to dentally realize said color key or shade guide and to refine or improve the choice of color by using a digital image of the neighboring tooth. In this connection EP 2 259 034 A1 and corresponding US published application No. 20100303315, which is hereby incorporated by reference, disclose a dental color key or shade guide and how to improve the tooth color of the replacement tooth with electronic support.

It has also already been proposed to further analyze the detected image of the neighboring tooth by rasterizing or scanning thereof and by dividing it into sections whose individual color and brightness values are determined in order to thus improve the distribution of the color and brightness values across the tooth.

Especially in the front tooth area the methods proposed so far, however, do not lead to optimal results, and the result strongly depends on the skill of the dental technician involved to define a harmonic coloring of the replacement tooth, i.e., the dental restoration part.

SUMMARY

Embodiments of the invention are based on the object of developing a method for producing a dental restoration part and a CAD/CAM device in accordance with the claims, which are hereby incorporated by reference.

According to embodiments herein, the method and device may be used for all teeth, preferably, front teeth, but also molars and premolars.

According to further embodiments, it is provided to also determine the virtual restoration part that is to be produced, in particular a replacement tooth, in the third dimension relative to the tooth surface by also recording the data of the neighboring teeth in the third dimension. The third dimension here refers to the direction perpendicular to the tooth surface.

Alternatively, it is also possible to define a three-dimensional coordinate system having an X, Y and Z coordinate. The Y-coordinate for example may then extend parallel to the tooth axis.

The X-axis then extends perpendicular to said Y coordinate, that is to say approximately parallel to the tooth surface in the horizontal direction. It is to be understood that in this case the X coordinate for each tooth considered is somewhat differently aligned. The Z coordinate then extends perpendicularly to the X and Y coordinate corresponding to the depth mentioned before, then extends perpendicular to the X and Y coordinate, that is to say in the labial-palatal direction in the upper jaw and in the labial-lingual direction in the lower jaw, respectively.

According to the invention it is suitably provided to produce and use stereometric data of the neighboring tooth or the neighboring teeth or of a tooth stump of the tooth that is to be replaced. The generation of stereometrically obtained data may for example be achieved with the aid of two digital cameras that are arranged at an angle with respect to one another and that are directed towards the same tooth, but for example also with the aid of a single digital camera that successively takes pictures at two different angles. The generation of stereometric data from two digital images that displays the same object from two different perspectives, of course is known per se and is inventively employed in order to be able to use the data.

The data generated in this way represents a three-dimensional copy of the mapped or recorded tooth, neighboring tooth or tooth stump. Apart from the photographically recorded data of the neighboring tooth or the tooth stump also a "virtual tooth" may be used, for example based on a dental restoration part that has already been produced once and that is then used with respect to the data set, wherein it is to be understood that it is also possible to modify the existing data with respect to tooth color and/or color distribution for example.

In an advantageous embodiment according to the invention it is also possible to use the existing data in the Z-axis of an already produced dental restoration part and to combine the data with the two-dimensionally produced data of a neighboring tooth or the tooth stump of the tooth that is to be replaced.

In an advantageous embodiment, the two neighboring teeth of the tooth to be replaced are used and are recorded photographically.

For the recordation of the stereometric data it is favorable if the two positions at which the pictures are taken, merely differ from each other in the X-coordinate. This simplifies the calculation of the stereometrically obtained data since then no further conversion of the data with respect to the Y-coordinate is required.

In order to realize this in practice, it is favorable to first define a precise plane of reference in which the pictures are taken. The plane of reference must refer to the head of the patient, that is to say in the case of lower jaw restorations to the lower jaw, and in the case of upper jaw restorations to the upper jaw, respectively. In order to make this easier, it is possible in a favorable embodiment to mark an auxiliary point in the mouth area of the patient, or, if necessary, a horizontal line that is directed to the X-direction, which line enables pictures to be taken with a horizontal accuracy of less than 5 percent, for example approximately 1 percent.

According to a further embodiment of the invention, it is particularly favorable that based on the stereometrically achieved three-dimensional data, three-dimensional sections are inventively produced. The size of the sections may be adapted to the requirements in whatever way required and in broad areas. The edge lengths in the three dimensions may differ from each other, but each section can also have the shape of a cube, that is to say it may comprise identical side or edge lengths in all three dimensions. For example, the edge length in the X-direction may amount to one third to one fiftieth part of the tooth width of the dental restoration part, in the Y-direction to one fourth to one fiftieth part of the height of the tooth to be replaced, and in the Z-direction to one third to one twentieth part of the tooth to be replaced.

Accordingly, each section is typically block-shaped and has the same tooth color (A1, B2 etc.). "Tooth color" refers both to the chroma values, brightness values, and translucency values of the dental material that is used for the restoration.

It is to be understood that the inventive provision of a dental restoration part is possible both with the aid of ceramic dental materials and plastic dental materials, or also with the aid of hybrid dental materials, wherein it is inventively preferred to use the dental materials according to the type of a Rapid-Prototyping process and to hereby build up the replacement tooth.

In an advantageous embodiment, for example, it is possible to build up the dental restoration part in layers with the aid of a rapid prototyping process, but it is also possible to use one of the following other possible methods instead of the layer-by-layer construction by means of 3D plotting or 3D printing:

Fused Deposition Modeling (FDM),
Laminated Object Modeling (LOM),
Ink-Jet Printing (IJP),
Selective Laser Melting (SLM),
Selective Laser Sintering (SLS), or
Stereolithography (STL or SLA)

For the implementation of the Rapid Prototyping process it is necessary to process the color data that is present in three-dimensional form and to convert the data into machine-readable data. The conversion is especially simple if the coordinate allocation is maintained between the CAD implementation, i.e., between the provision of the color data and the CAM device, i.e., the device for producing the dental restoration part, according to a rapid prototyping process, so that the replacement tooth is produced with the same coordinates as during the recording of the neighboring teeth.

According to further embodiments of the invention it is favorable to adjust the data rates to the produced sections, but also to the CAM device. For sections in this sense, the term voxel has been used, so that in this respect isotropic voxels are present. If a 3D printing process, for example, is employed, the droplet size of the CAD-device can then determine the size of the sections.

According to another embodiment of the invention it is preferable to use the same tooth color for each section. In the case of very large sections such as in the case of an edge length of half the tooth thickness in the Z-direction, however, it is also possible to provide one of the parameters, for example, the translucency, in one of the coordinates, for instance, in the direction of the Z-coordinate, with a gradient so that the translucency near the surface is greater and in the tooth interior, it is less. It is to be understood that this is only possible if during the rapid prototyping application process the droplet size is smaller than the section size so that the desired differentiation may then be implemented.

It is preferred, however, to keep the color data parameter within the section constant.

During the CAD step any influence on the part of the user may be realized. In this way for example, the 3D model of the tooth that is to be produced, can be represented on a display in a manner known per se and can be changed in the space, thus be tilted, turned and zoomed.

Moreover, parameters of the color data of the section may be changeable in any desired manner. This can take place before the rendering step so that for example in adaptation to the exposure or light situation, the brightness or chroma values are adjusted during the stereometric recording. For a subset of the produced voxels, however, this can also occur after the rendering step by providing, for example, the translucency values in the direction of the Z-axis with a negative gradient and thus the translucency is reduced.

According to more embodiments of the invention, it is particularly favorable if there is a data base that is composed of virtually or really generated data of replacement teeth and natural teeth. Human teeth comprise a certain deviation margin of distribution with respect to the parameters of the color data, and indeed both with respect to chroma values and brightness as well as nd translucency values. Here the focus lies on recording the most frequently distributed color data in the data base in order to enable a basis for the adaptation of the determined color data to natural teeth.

It is also possible to provide the data base based on a rough distribution of the parameter values of the data of a natural tooth, that is to say to take a voxel edge length of one millimeter as a basis for example, and to simultaneously use this raster as a basis in order to be able to easier realize the sections with an edge length of one tenth mm for example which are to be produced via CAD design.

In this respect the data of neighboring "rough voxels" can be quickly determined for producing the "fine voxels" and a gradient may be placed across the 10 "fine voxels," regarded in one coordinate direction, in order to enable a finer distribution.

In a particularly favorable manner according to the invention, some kind of feed back during the generation of virtual data for the dental restoration part is possible, also.

During the CAD design, the tooth to be produced may be simulated and represented on the screen. If the screen is calibrated with respect to the color rendering, the appearance of the virtual tooth may be compared to the image of the neighboring tooth in order to achieve a realistic impression. If the result is still not satisfactory, the layer thickness or translucency, for example, may then be adjusted, and it is also possible to conduct a new rendering operation before CAM manufacturing of the dental restoration part such that no actual dental restoration part is necessary for comparison to neighboring teeth.

Further it is also possible to mathematically compensate for shrinkage values in the CAM process used already in advance. Both during the sintering or firing of ceramic green bodies and during the polymerization of curable plastic materials a shrinkage factor is known per se that may be determined and corrected in advance.

For optimization it is also possible to prepare a sample tooth with the aid of the used process in advance, then to sinter or harden it, and if necessary, to wear out the tooth artificially, and then to determine the amount of shrinkage compared to the original or source data. If it is found then that the shrinkage is different in the three space coordinates, this may also be compensated according to the invention by means of a simple conversion between the actually produced parameter and the target which give three shrinkage factors in the direction of the three coordinates.

In an advantageous embodiment it is preferable that upon determination of the dental colors at least one section or a plurality of sections from the set of three-dimensional sections is displayed on a screen and is selected, and the surface color of the selected section or of the selected sections is compared to the stored tooth colors that are stored in a layering database, wherein on said screen in particular the tooth color detected, the colors of the individual layer materials, the thickness of the individual layers, the thickness of the incisal material and/or the translucency in percent are represented in a spatially associated manner with respect to the respective section.

In an advantageous embodiment it is preferable that a determination of the tooth colors is performed when selecting the one or more sections, and that the respective tooth color of the one or more sections is stored in a work table by confirming on the screen, said work table forming the base for the CAM production of the dental restoration part.

In an advantageous embodiment it is preferable that the color data is produced by creating a three-dimensional color photo, wherein at least two different positions of cameras and/or two cameras from different angular positions take a photo of a neighboring tooth and/or a tooth stump for the dental restoration part, which color photos are stereometrically superimposed thereby creating a 3D image.

In an advantageous embodiment it is preferable that the created three-dimensional color photo is rendered, and the virtual dental restoration part is simulated on the display and is compared to the color photos of the neighboring tooth.

In an advantageous embodiment it is preferable that the three-dimensional sections are united in layers and the thickness of the layers, the transparency thereof and the material selection is adjusted after optical comparison with the neighboring tooth, and is rendered again, if necessary.

In an advantageous embodiment it is preferable that the size of the three-dimensional sections and/or the thickness of the layers is enlarged by one correction factor that takes into account empirical values during the solidification of the dental material and the shrinkage arising at this position.

In an advantageous embodiment it is preferable that the dental material that is used for solidification, is at least partially polymerizable and is polymerized, and in particular that in the case of using Ink-Jet-Printing as a Rapid-Prototyping Process, the solidification takes place through cooling down.

In an advantageous embodiment it is preferable that the dental material is provided in the form of ceramic green bodies that are sintered for solidification.

In an advantageous embodiment it is preferable that the creation of the virtual dental restoration part is performed by using a data base in which different tooth shapes and/or tooth runs are presented in a three-dimensionally stored form, based upon which layers are configured.

In an advantageous embodiment it is preferable that the CAD/CAM device for the production of a dental restoration part is based on geometrical data that determine the geometrical shape of the dental restoration part to be produced, and is based on color data that characterize the dental restoration part to be produced and are generated from either a tooth data base or a neighboring tooth of the dental restoration part to be produced and/or the tooth stump thereof, and that the device stereometrically detects the color data three-dimensionally and divides the color data generated into a plurality of individual, three-dimensional sections extending through the restoration part; and that the device based thereon determines layers of dental material from which the dental restoration part is to be produced; and that for the at least one section and/or the plurality of united sections tooth colors (A1, B2 etc.) are determined manually or automatically and are stored in a work table, that the tooth color data is transferred to a CAM device and based thereon the dental restoration part is built up in layers and is subsequently cured.

In an advantageous embodiment it is preferable that the device comprises a display with a cursor, and the three-dimensional sections may be represented on the display and may be selected, and that based on the selection a comparison of the surface color with stored tooth colors of a layering data base is effected and thereby different parameters of sections may be represented on the display and may be confirmed for providing the CAM data.

In a further advantageous embodiment it is preferable that the device comprises a digital camera that detects the color data at two positions which differ from each other in the horizontal direction and which are located at the same vertical height in the vertical direction, or which differ in the vertical direction and are located at the same position in the horizontal direction.

In a further advantageous embodiment it is preferable that the stereometrically detected colors may be provided in two dimensions with the aid of taken pictures, or in the third dimension, in particular in the direction of the Z-coordinate, with the aid of already existing data, in particular with the aid of an already existing dental restoration part.

BRIEF DESCRIPTION OF THE DRAWINGS

Embodiments of the present invention will be more fully understood and appreciated by the following Detailed Description in conjunction with the accompanying drawings, in which.

DETAILED DESCRIPTION

Figure 1:
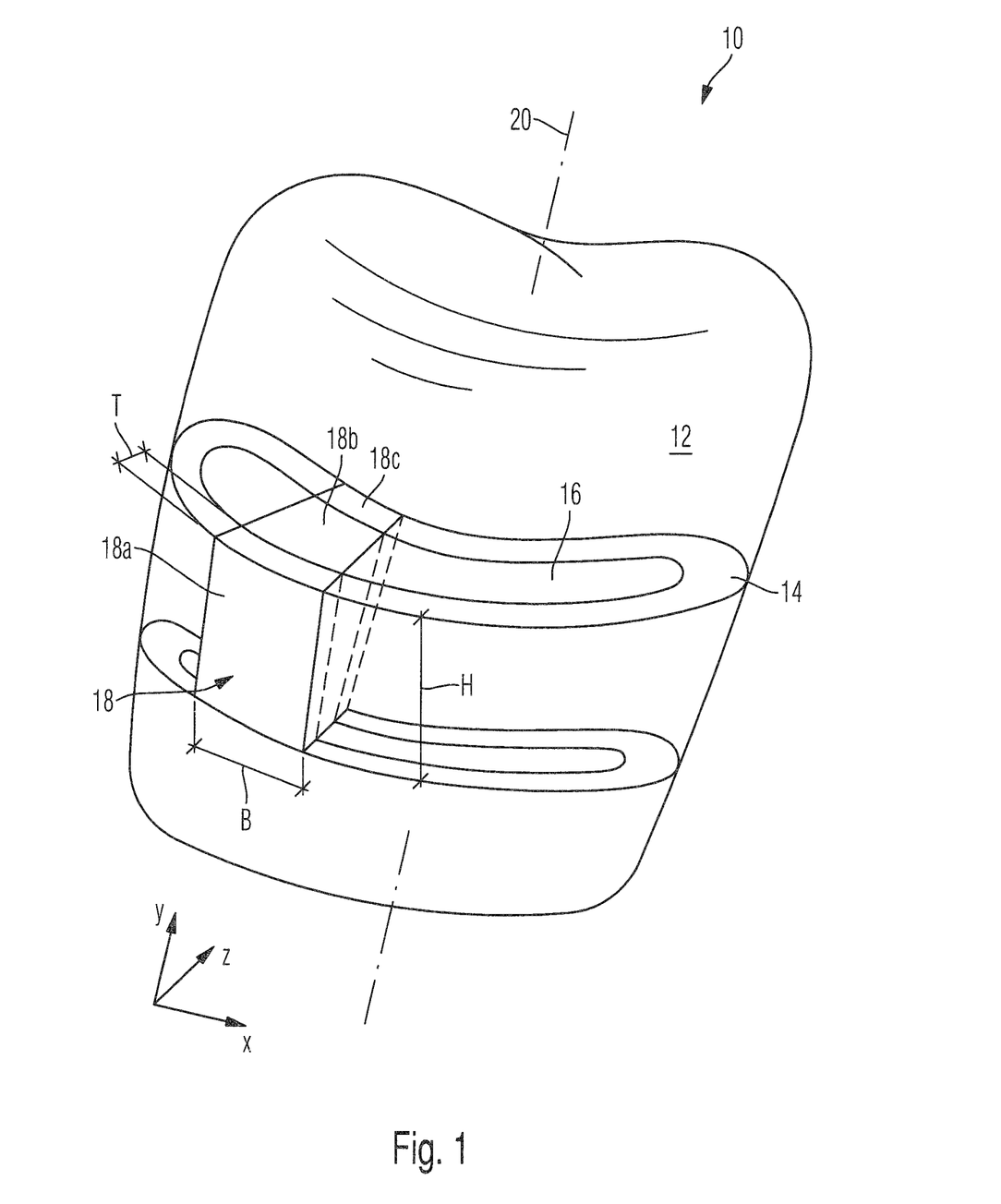
FIG. 1 illustrates a schematic three-dimensional representation of a virtual replacement tooth or dental restoration part in one embodiment of the invention.

In the representation according to FIG. 1 a virtual tooth is apparent that has been produced as a dental restoration part and can then be accordingly displayed on a screen. The replacement tooth 10 is embodied as an incisor in the illustrated embodiment, wherein, however, an implementation with a premolar or even a molar is possible likewise.

In a manner known per se, the replacement tooth 10 adjacent to its tooth surface 12 comprises the enamel material that extends with a thickness in the range of a few millimeters along the tooth surface 12.

In a matter known per se, dentin material 16 extends within the enamel material, with the layer thickness of the enamel material 14 across its extension somewhat changing both in X-direction and Y-direction, but not very strongly.

The thus existing structure of the replacement tooth is now provided by determining sections 18 which in FIG. 1 are represented greatly enlarged for the purpose of clarity, and which in practice, however, are substantially smaller. The section 18a is provided in the area of the enamel material 14 and substantially extends in a square-cut shape with a height H that approximately amounts to one-and-a-half times a width B. The height H corresponds to the edge length in the direction of the Y coordinate, and the width B corresponds to the edge length of the section 18a in the direction of the X coordinate.

The section 18a also comprises a depth T, thus an edge length in the direction of the Z coordinate that in turn is substantially smaller than the width B, for example amounts to one third of the width B.

The section 18a is defined with respect to its tooth color, and in fact based on stereometrically recorded data of the neighboring teeth or the neighboring tooth.

Figure 3:
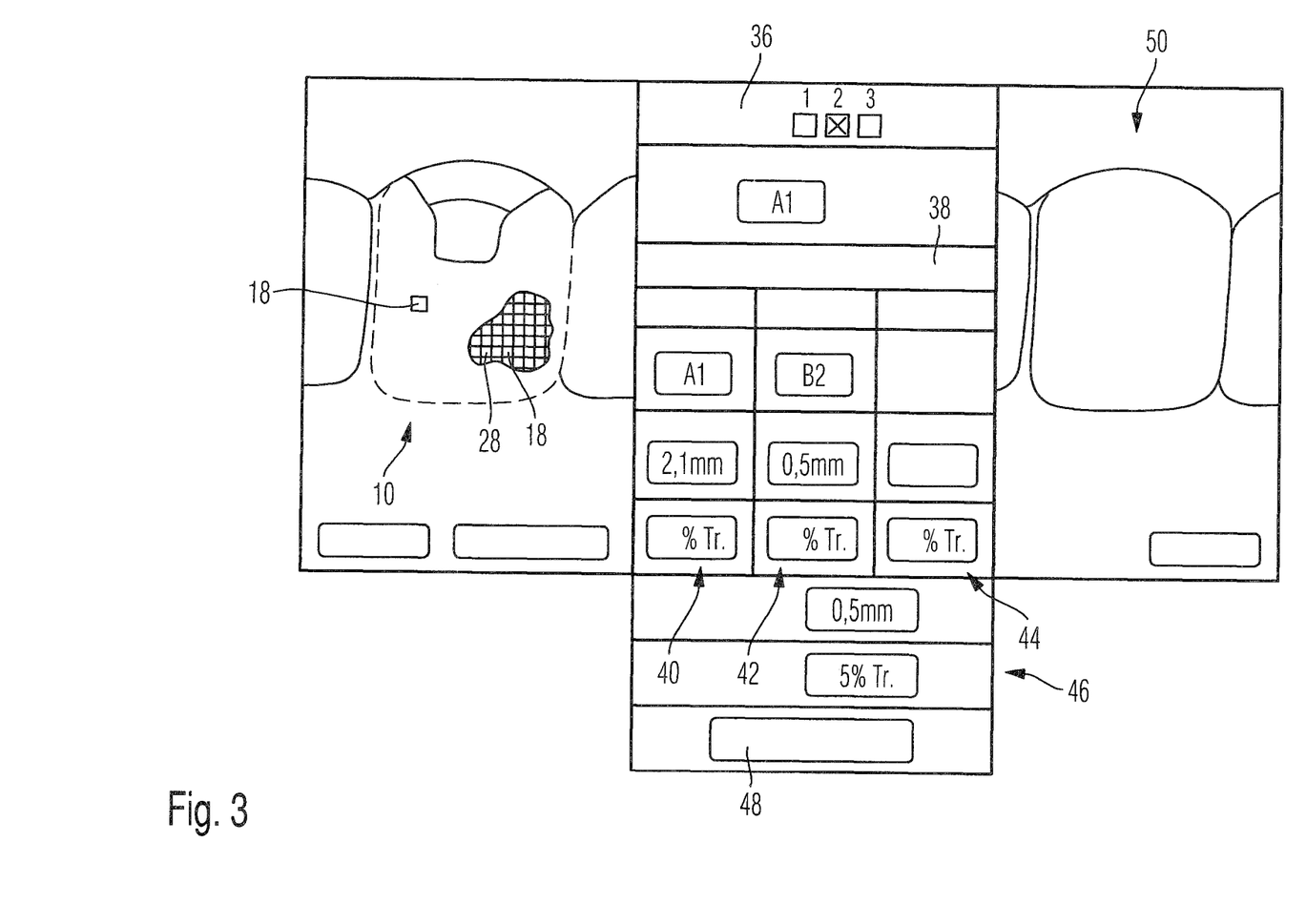
FIG. 3 illustrates a representation of an intermediate step of the inventive CAD/CAM process including an auxiliary screen and the presentation thereof.
Figure 4:
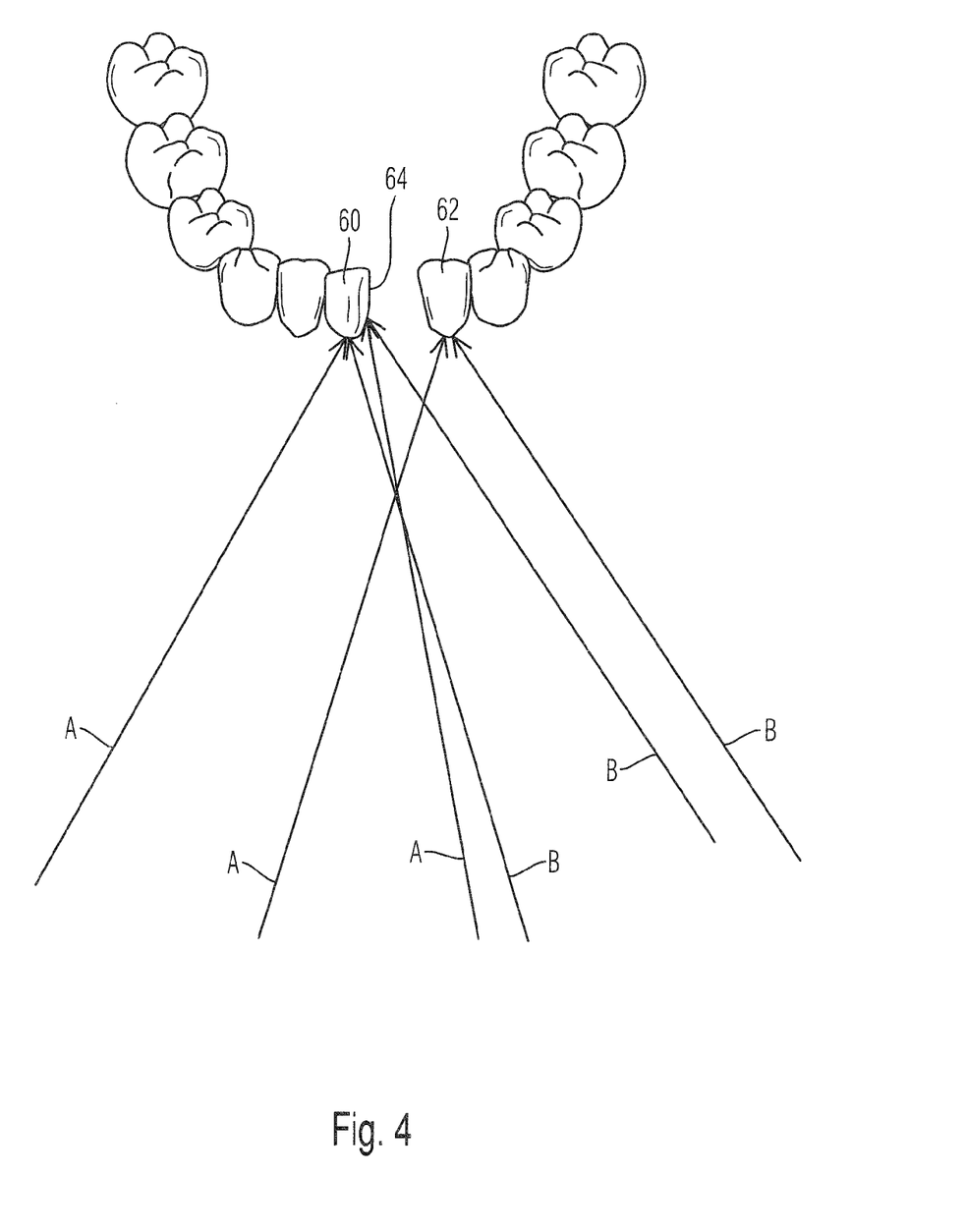
FIG. 4 illustrates a schematic representation of the arrangement for detecting the stereometric color data of neighboring teeth.

For the provision of data with respect to the tooth color of section 18a, a stereometric process is used that is schematically shown in FIG. 4. Following the collection of data, the data is further adapted by means of a CAD device shortly described in FIG. 3.

Each of the sections 18 is determined with respect to the parameters of the tooth colors, thus with respect to its brightness value, its chroma value and its translucency value. Prior to the production of the replacement tooth, the replacement tooth is represented on the display of the CAD device in a corresponding manner, please compare FIG. 3.

Apart from the section 18a, further sections 18b and 18c are apparent in FIG. 1, with section 18b extending in the area of the dentin and section 18c on the other hand extending in the enamel region that is opposite to the section 18a in relation to the tooth 10.

It is to be understood that the tooth colors of these three sections are typically different, and also that typically substantially more than merely three sections are provided in a correspondingly large area of the replacement tooth 10.

The sections according to the type of voxels extend three-dimensionally through the replacement tooth 10. In practice, a thousand or even ten thousand voxels per replacement tooth 10 may be realized by all means. The extension of the sections 18 respectively takes place so that they border on each other. Adjacent sections are selected separately from each other with respect to the tooth colors according to the rendering result of the stereometric digital recordings of the neighboring teeth according to FIG. 4.

With the aid of developing and opening the third dimension, that is to say the Z axis through the inventive stereometric recording, the depth effect of replacement teeth, especially in the region of the enamel material, may be strongly improved and is essentially more close to nature than it was possible with processes known so far.

Based on the stereometrically recorded data, a conversion into stereometric data is conducted according to the invention, that is to say data in the X-, Y- and Z-direction. For each voxel, namely for each section 18, the corresponding parameters are determined by conducting three-dimensional rendering. In this connection, the section size and size distribution may be adjusted during the rendering operation if necessary, even if the most simple mathematical solution is to operate with identical size of the individual voxels.

Figure 2:
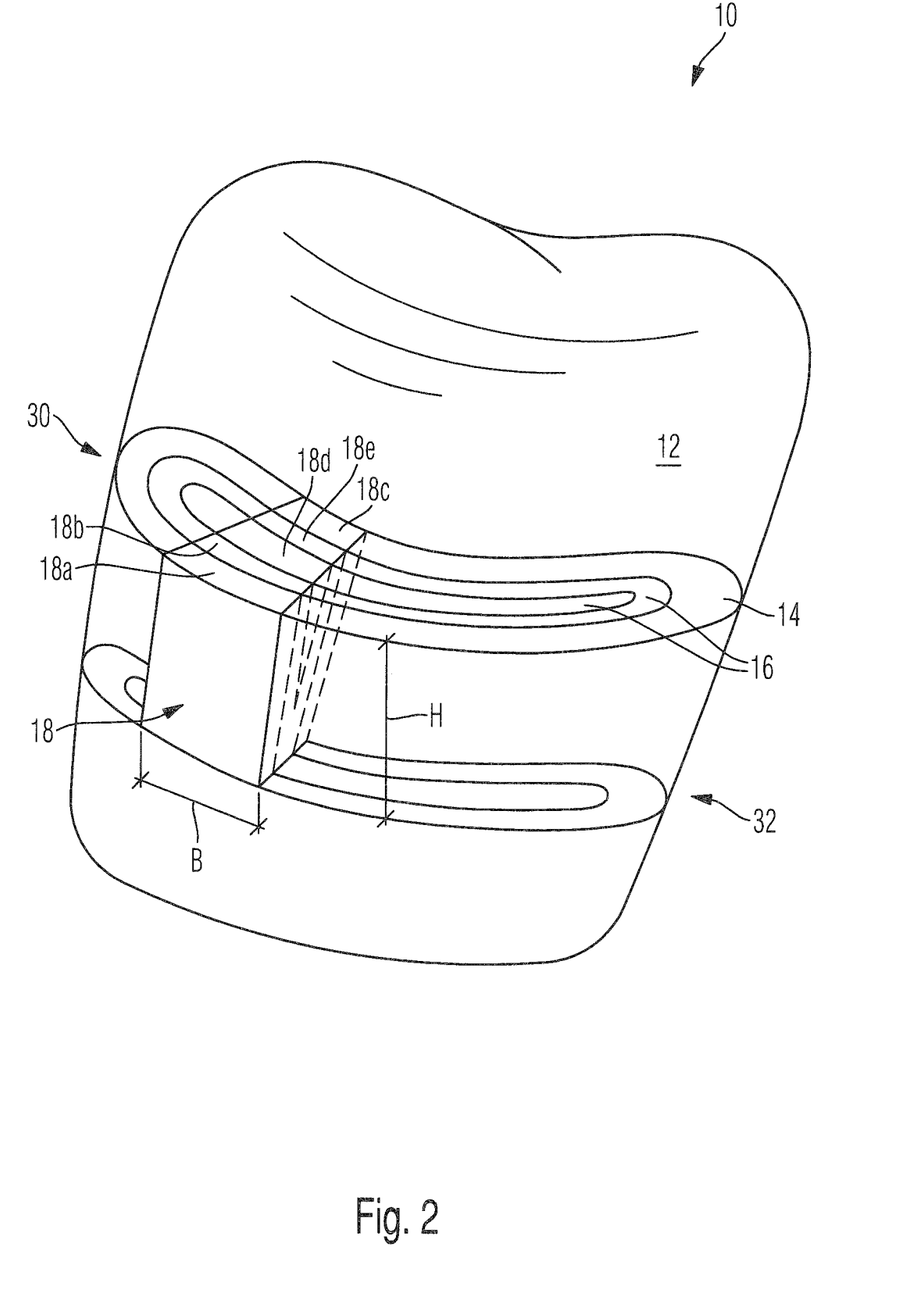
FIG. 2 illustrates a further embodiment of the virtual dental restoration part according to FIG. 1.

While the sections are substantially block-shaped in the embodiment according to FIG. 1, this is not the case in the embodiment according to FIG. 2. Here, the edge lengths in the depth direction, thus in the direction of the Z coordinate, are reduced, and since the dentin layer 16 of an incisor changes across its axis 20 of the tooth, more sections are provided here in an upper area 30 of the tooth 10 than in a lower area 32 of the replacement tooth 10.

This is schematically denoted by section 18d that tapers to a point at the bottom. In fact, the number of sections is substantially larger than illustrated in the figures, as it has already mentioned before, and the number of sections for example is reduced from 20 to 16, if regarded between the area 30 and the area 32, in order to reproduce the corresponding dimensional change in the direction of the Z-coordinate.

A section distribution that approaches the actual resolution, is apparent in FIG. 3 in the left part of the display illustrated there. The replacement tooth is schematically illustrated there in order to realize the 3-D design, wherein it is possible to select a field 28 of sections with the cursor that can then be treated together.

Instead, also a single section 18 can be determined by the cursor selection, as it is illustrated somewhat further left in FIG. 3 in the left area of the display.

In a manner known per se, in the middle region the tooth color that has been determined first, for example A1, is indicated when the cursor is located at the respective section.

In an upper operator panel 36 of the middle region of the screen according to FIG. 3 it is possible to select the layering in order to be able to simultaneously influence the tooth colors of several sections. To simplify matters, merely 3 layers may be selected and it goes without saying that in practice substantially more layers may be realized as well.

In an operator panel 38 it is possible to conduct a layering correction. A first layer 1 may be treated in a column 40, a second layer 2 may be treated in a column 42 and a third layer 3 may be treated in a column 44. In the upper row at first the tooth color A1, B2 etc. may be displayed and changed, in a second row the thickness of the layer such as 2.1 mm for layer 1, 0.5 mm for layer 2 and no fixed value for layer 3. The fact that the thickness of layer 3 is not fixed in this respect according to the invention means that the remainder to the total thickness of the tooth in the Z direction is filled up there.

In the third row in a further field in each column, respectively, the translucency may be determined and changed if necessary.

Further operator fields 46 are provided below the middle area that enable the common influence on the layers and that change them proportionally, for example with respect to translucency.

With the aid of a further operator field 48, a detailed rendering of the selected area may then be conducted.

The result of the changes is illustrated in a right area 50 of the screen according to FIG. 3. The screen by the way may be designed as a touch screen or as a screen that may be operated by means of a cursor in order to provide the desired CAD functions and thus the 3D design.

In the area 50 the finished tooth is illustrated in the rendered form and the expected result may be evaluated in advance, that is, before the CAM manufacture. In this connection it is also possible to repeat the rendering operation with differently selected parameters of the tooth color, but also with different section sizes and/or translucency values.

FIG. 4 shows schematically in which manner neighboring teeth may be employed in order to identify the desired data. For each detection point, in a stereometric manner known per se, one digital image each is taken at various angles. For each point exist the two positions A and B, respectively, that form a different angle with the region of the tooth 60 or 62, respectively, that is to be detected.

Even if the detection of merely the surface of the respective tooth 60 is illustrated here, it is to be understood that in fact due to the translucency, of particularly, the enamel mass of the neighboring tooth 60, in fact the depth effect is captured by the stereometric image and is inventively exploited in order to provide the third dimension during the production of the dental restoration.

According to the invention it is also favorable that even an area 64 of the neighboring tooth 60 that extends somewhat further in the palatal area, can be determined by utilizing the tooth space so that in this respect the rearward areas of the respective incisor can be determined and can be used for the new production of the replacement tooth.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method for producing a dental restoration part from a virtual restoration part using geometrical data of the virtual restoration part, comprising:
    generating color data as three-dimensional, stereometrically generated data based on at least a tooth to be restored or replaced, one or more neighboring teeth of the tooth to be restored or replaced, or a tooth stump of the tooth to be restored or replaced;
    dividing the color data into a plurality of individual, three-dimensional sections extending through the virtual restoration part;
    determining the differences of the sections with respect to individual color parameters and allocating tooth colors to be used;
    conditioning and storing the tooth colors;
    converting the tooth colors into machine-readable data for the production of the dental restoration part;
    transferring the machine readable data to a computer assisted manufacturing (CAM) device;
    building the color-adjusted dental restoration part in layers using dental material of different tooth colors,
    wherein the color data is produced by creating a three-dimensional color photo, wherein at least two different positions of at least one camera from different angular positions take a photo of a neighboring tooth and/or a tooth stump for the dental restoration part, which color photos are stereometrically superimposed thereby creating a 3D image, wherein the created three-dimensional color photo is rendered, and the virtual dental restoration part is simulated on the screen and is compared to the color photos of the neighboring tooth, and
    wherein the virtual dental restoration part is adjustable with respect to thickness, transparency, and material selection after optical comparison with the neighboring tooth, and when the optical comparison does not meet a predetermined criteria, the virtual dental restoration is rendered again, until the comparison meets the predetermined criteria, before CAM manufacturing of the dental restoration part such that no actual dental restoration part is necessary for comparison to neighboring teeth.

2. The method of claim 1, wherein the dental material is subsequently cured or solidified.

3. The method of claim 2, wherein the geometrical data comprises at least one of a spatial dimension, a position or a volume of the restoration part.

4. The method as claimed in claim 1, wherein, upon determination of the tooth colors to be used, at least one section or a plurality of sections from the set of three-dimensional sections is displayed on a screen and is selected; and
    the tooth colors of the selected section or of the selected sections is compared to stored tooth colors that are stored in a layering database;
    wherein on said screen, a tooth color detected, colors of individual layer materials, thickness of the individual layers, thickness of incisal material and/or translucency in percent are represented in a spatially associated manner with respect to the selected section.

5. The method as claimed in claim 4, wherein a determination of the tooth colors is performed when selecting the one or more sections, and the respective tooth color of the one or more sections is stored in a work table by confirming on the screen, said work table forming the base for the CAM production of the dental restoration part.

6. The method as claimed in claim 1, wherein the size of the three-dimensional sections and/or the thickness of the layers is enlarged by one correction factor that takes into account empirical values during the solidification of the dental material and the shrinkage arising at a position.

7. The method as claimed in claim 6, wherein the dental material that is used for solidification, is at least partially polymerizable and is polymerized.

8. The method as claimed in claim 7, wherein the building of the restoration is performed by a Rapid-Prototyping Process.

9. The method as claimed in claim 8, wherein the Rapid-Prototyping Process comprises Ink-Jet-Printing and the solidification takes place through cooling down.

10. The method as claimed in claim 9, wherein building the dental restoration forms a ceramic green body that is sintered for solidification.

11. The method as claimed in claim 9, wherein the creation of the virtual dental restoration part is performed by using a data base in which different tooth shapes and/or tooth runs are presented in a three-dimensionally stored form, from which the layers are configured.

12. A CAD/CAM device for the production of a dental restoration part based on geometrical data, wherein the geometrical data determines the geometrical shape of the dental restoration part to be produced, are based on color data that characterize the dental restoration part to be produced; and are generated from either a tooth data base or a neighboring tooth of the dental restoration part to be produced and/or the tooth stump thereof, wherein the device comprises
    a first component that stereometrically detects the color data three-dimensionally;
    a second component that divides the color data generated into a plurality of individual, three-dimensional sections extending through the restoration part;
    a third component that determines layers of dental material from which the dental restoration part is to be produced;
    a fourth component that determines manually or automatically for the at least one section and/or the plurality of united sections, tooth colors;
    a fifth component for storing the tooth colors in a work table as tooth color data;

a sixth component for transferring the tooth color data to a CAM device; and a seventh component for building up the dental restoration part in layers;

wherein the first component comprises at least one digital camera that detects the color data at two positions, said positions differing from each other in a horizontal direction and being located in a vertical direction at the same vertical height, or differing in the vertical direction and being located at the same position in the horizontal direction; and wherein the device comprises a display with a cursor and the three-dimensional sections are represented on the display and are selected, and in that based on the selection a comparison of a surface color with stored tooth colors of a layering data base is effected and thereby different parameters of sections are represented on the display and are confirmed or adjusted with respect to thickness, transparency, and material selection after optical comparison with a neighboring tooth, and when the comparison does not meet a predetermined criteria, the different parameters are rendered again until the comparison meets the predetermined criteria, before CAM manufacturing of the dental restoration part such that no actual dental restoration part is necessary for comparison to neighboring teeth.

13. The CAD/CAM device as claimed in claim 12, further comprising an eighth component for curing or solidifying the layers.

14. The CAD/CAM device as claimed in claim 12, wherein the stereometrically detected colors may be provided in two dimensions with the aid of taking pictures, or in a third dimension, in the direction of the Z-coordinate, with aid of already existing data.

15. The CAD/CAM device as claimed in claim 14, wherein the already existing data is from an already existing dental restoration part.

16. The CAD/CAM device as claimed in claim 12, wherein the first component comprises one or two digital cameras.

17. The CAD/CAM device as claimed in claim 16, wherein the one digital camera is positioned on at least two different positions.

18. The CAD/CAM device as claimed in claim 16, wherein two digital cameras are positioned at different angular positions.

19. The CAD/CAM device as claimed in claim 12, wherein second through sixth components are the same component and comprise a CAD database.

20. The CAD/CAM device as claimed in claim 12, wherein third and fourth components comprise a layering database.

21. The CAD/CAM device as claimed in claim 12, wherein the seventh component comprises a CAM device.

22. The CAD/CAM device as claimed in claim 21, wherein the CAM device comprises a rapid prototyping device.

23. The CAD/CAM device as claimed in claim 22, wherein rapid prototyping device comprises an ink-jet printing device.

24. The CAD/CAM device as claimed in claim 12, wherein the eighth component comprises a polymerization device or sintering furnace.

* * * * *